United States Patent
Montoya et al.

(10) Patent No.: US 11,147,752 B2
(45) Date of Patent: *Oct. 19, 2021

(54) SKIN-TIGHTENING COMPOSITION

(71) Applicant: L'Oreal, Paris (FR)

(72) Inventors: Mariana Montoya, Berkeley Heights, NJ (US); Angelike Galdi, Westfield, NJ (US); Susan Halpern, Basking Ridge, NJ (US); David Chan, Edison, NJ (US)

(73) Assignee: L'OREAL, Paris (FR)

( * ) Notice: Subject to any disclaimer, the term of this patent is extended or adjusted under 35 U.S.C. 154(b) by 83 days.

This patent is subject to a terminal disclaimer.

(21) Appl. No.: 16/398,648

(22) Filed: Apr. 30, 2019

(65) Prior Publication Data

US 2020/0345595 A1 Nov. 5, 2020

(51) Int. Cl.
*A61K 8/06* (2006.01)
*A61K 8/25* (2006.01)
*A61K 8/37* (2006.01)
*A61K 8/34* (2006.01)
*A61Q 19/08* (2006.01)

(52) U.S. Cl.
CPC ............ *A61K 8/062* (2013.01); *A61K 8/25* (2013.01); *A61K 8/345* (2013.01); *A61K 8/375* (2013.01); *A61Q 19/08* (2013.01); *A61K 2800/262* (2013.01); *A61K 2800/48* (2013.01); *A61K 2800/5922* (2013.01)

(58) Field of Classification Search
CPC .......... A61K 8/062; A61K 8/25; A61K 8/345; A61K 8/375; A61K 2800/262; A61K 2800/48; A61K 2800/5922; A61Q 19/08
See application file for complete search history.

(56) References Cited

U.S. PATENT DOCUMENTS

| | | | |
|---|---|---|---|
| 4,255,416 A | 3/1981 | Gillespie | |
| 4,599,379 A | 7/1986 | Flesher et al. | |
| 4,628,078 A | 12/1986 | Glover et al. | |
| 4,690,774 A * | 9/1987 | Vishnupad | A61Q 19/00 516/29 |
| 4,835,206 A | 5/1989 | Farrar et al. | |
| 4,849,484 A | 7/1989 | Heard | |
| 5,100,660 A | 3/1992 | Hawe et al. | |
| 6,497,860 B1 * | 12/2002 | Kawato | A61K 8/23 424/401 |
| 7,192,599 B2 | 3/2007 | Mercier et al. | |
| 9,095,543 B2 | 8/2015 | Susak et al. | |
| 2008/0181956 A1 * | 7/2008 | Ha | A61Q 19/00 424/489 |
| 2013/0189332 A1 | 7/2013 | Breyfogle | |
| 2013/0195783 A1 * | 8/2013 | Breyfogle | A61K 8/26 424/62 |
| 2014/0356302 A1 | 12/2014 | Yuen | |
| 2015/0016862 A1 | 1/2015 | Guay et al. | |
| 2015/0037380 A1 | 2/2015 | Newman et al. | |
| 2017/0189288 A1 | 7/2017 | Choiu et al. | |
| 2017/0189298 A1 | 7/2017 | Manning et al. | |
| 2017/0189299 A1 | 7/2017 | Manning et al. | |
| 2017/0189320 A1 | 7/2017 | Chiou et al. | |
| 2019/0105254 A1 | 4/2019 | Montoya et al. | |

FOREIGN PATENT DOCUMENTS

| | | | |
|---|---|---|---|
| EP | 228 868 A2 | 7/1987 | |
| EP | 0244859 A2 * | 11/1987 | A61K 8/25 |
| EP | 2 404 642 A2 | 1/2012 | |
| WO | 2013/109850 A2 | 7/2013 | |

* cited by examiner

*Primary Examiner* — Jianfeng Song
(74) *Attorney, Agent, or Firm* — Polsinelli PC

(57) ABSTRACT

Skin-tightening compositions for providing a physical tightening effect to the skin and methods for using the same. The compositions may be in the form of an oil-in-water emulsion and include about 0.1 wt. % to about 6 wt. % of sodium silicate; at least 3 wt. % to about 11.5 wt. % of magnesium aluminum silicate; about 1 wt. % to about 15 wt. % of one or more fatty compounds; about 0.1 to about 20 wt. % of one or more nonionic emulsifiers; about 1 to about 25 wt. % of one or more polyols; and about 50 to about 90 wt. % of water, wherein the weight percentages are based on the total weight of the composition. The weight ratio of the sodium silicate to magnesium aluminum silicate is from 0.08 to 1.0 and a total amount of sodium silicate and magnesium aluminum silicate is 3 wt. % to 13 wt. %.

17 Claims, No Drawings

SKIN-TIGHTENING COMPOSITION

FIELD OF THE INVENTION

Aspects of the invention relate to skin-tightening compositions and methods for using the same. In particular, the skin-tightening compositions disclosed herein provide a physical tightening effect to the skin and are useful for treating eye bags, facial wrinkles, and other age-related skin imperfections.

BACKGROUND OF THE INVENTION

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Attempts have been made to develop new categories of products to improve the appearance of skin without the drawbacks of existing products and procedures. One such family of products can be generally classified as "adhesive, contractile film formers." Film formers are chemical compositions that when applied to skin, leave a pliable, cohesive and continuous covering. A select group of film formers are also adhesive to the skin and contractile.

Compositions containing sodium silicate have been found to have dramatic, instant results. However, typical compositions containing sodium silicate quickly lose their skin tightening effect. For example, the films lose their elasticity and quickly begin to whiten, crack, and peel. Users may experience irritation and/or itchiness as certain films lose their elasticity and begin to crack and peel. Accordingly, there is a long standing need for new and improved long-lasting skin tightening compositions that do not suffer the drawbacks of other skin-tightening compositions.

SUMMARY OF THE DISCLOSURE

Aspects of the invention relate to skin-tightening compositions and methods for using the same. In particular, the skin-tightening compositions disclosed herein provide a physical tightening effect to the skin and are therefore useful for treating eye bags, facial wrinkles, and other age-related skin imperfections. The skin-tightening compositions disclosed herein advantageously provide an instant tightening treatment, which may include both sensational and physical tightening without many of the drawbacks of products currently on the market, such as whitening, cracking, and/or peeling.

It is commonly expected that if the skin-tightening composition contains 1% or more of polyvalent silicate, the film formed by the skin-tightening composition is prone to cracking, which may lead to peeling and increased whitening effects. Skin-tightening compositions according to aspects of the invention, however, include at least 3 wt. %, and preferably at least 4 wt. %, of magnesium aluminum silicate, a polyvalent silicate. Surprisingly, these skin-tightening compositions form films that exhibit improved tightening effects with reduced whitening effects. While not wishing to be bound by any particular theory, skin-tightening compositions produced in accordance with aspects of the invention overcome many of the drawbacks from commercially available skin-tightening products by providing a synergistic combination of sodium silicate and magnesium aluminum silicate in proportions and amounts discussed herein. The skin-tightening compositions herein typically are in the form of an oil-in-water emulsion and include:

(a) about 0.1 wt. % to about 6 wt. % of sodium silicate;
(b) at least 3 wt. % to about 11.5 wt. % of magnesium aluminum silicate;
wherein the weight ratio of (a) to (b) is from 0.08 to 1.0 ((a)/(b)) and a total amount of sodium silicate and magnesium aluminum silicate is 3 wt. % to 13 wt. %;
(c) about 1 wt. % to about 15 wt. % of one or more fatty compounds;
(d) about 0.1 wt. % to about 20 wt. % of one or more nonionic emulsifiers;
(e) about 1 wt. % to about 25 wt. % of one or more polyols; and
(f) about 50 wt. % to about 90 wt. % of water,
wherein the weight percentages are based on the total weight of the composition.

The skin-tightening compositions are preferably formulated to form a transparent film when applied to the skin. The skin-tightening composition may, preferably, have a ratio of sodium silicate to magnesium aluminum silicate that is from 0.1 to 1.1. The sodium silicate used in the skin-tightening compositions may be chosen from sodium othosilicate, sodium metasilicate, sodium pyrosilicate, and a mixture thereof.

Non-limiting examples of the one or more fatty compounds include those chosen from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In one instance, the fatty compound(s) include one or more fatty acid triglyceride(s), such as caprylic/capric triglyceride.

Non-limiting examples of the one or more nonionic emulsifiers include those chosen from polyglyceryl-based emulsifiers, polyol esters, glycerol ethers, oxyethylenated and/or oxypropylenated ethers, ethylene glycol polymers, sorbitan esters, and a mixture thereof. In some cases, the nonionic emulsifier(s) includes one or more polyglyceryl-based emulsifiers. The one or more polyglyceryl-based emulsifiers may be chosen from polyglyceryl 10-stearate, polyglyceryl-3-caprate, polyglyceryl-3-diisostearate, polyglyceryl-3 methylglucose distearate, and a mixture thereof.

The one or more polyols of the skin-tightening compositions are preferably chosen from polyols having from 2 to 15 carbon atoms and at least two hydroxyl groups. For example, the one or more polyols may be chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

The skin-tightening compositions may, in some instances, also include one or more thickening agents. The one or more thickening agents may be chosen from acryloyldimethyltaurate polymers, carboxylic acid polymers, crosslinked polyacrylate polymers, polyacrylamide polymers, polysaccharides, gums, and a mixture thereof. In some instances, the thickening agent includes one or more chosen from acryloyldimethyltaurate polymers chosen from acrylamide/sodium acryloyldimethyltaurate copolymer, acrylamide/sodium acryloyldimethyltaurate/acrylic acid copolymer, ammonium acryloyldimethyltaurate/beheneth-25 methacrylate crosspolymer, ammonium acryloyldimethyltaurate/carboxyethyl acrylate crosspolymer, ammonium acryloyldimethyltaurate/laureth-7 methacrylate copolymer, ammonium acryloyldimethyltaurate/steareth-25 methacrylate crosspolymer, ammonium acryloyldimethyltaurate/steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium acryloyldimethyltaurate/Steareth-20 methacrylate copolymer, hydroxyethyl acrylate/Sodium acryloyldimethyl taurate copolymer, polyacryloyldimethyltaurate polyoxymethylene melamine, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate, crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer, sodium polyacryloyldimethyl taurate, and a mixture thereof.

The skin-tightening compositions may be employed as part of a method for improving the appearance of skin by applying one of the skin-tightening compositions discussed herein to the skin. The methods may improve the appearance of skin by treating or reducing the appearance of wrinkles, blemishes, dryness, roughness, dullness, age spots, sagging, eye bags, and/or puffy skin. The methods may firm and/or tighten the skin by applying the skin-tightening composition to the skin.

DETAILED DESCRIPTION OF THE DISCLOSURE

Aspects of the invention are directed to cosmetic compositions that provide instantaneous and long-lasting tightening effects to the skin. For example, the skin-tightening compositions are particularly useful for providing a tightening effect to a user's skin under the eyes to treat eye bags, facial wrinkles, and other age-related skin imperfections. The skin-tightening compositions disclosed herein preferably provide an instant tightening treatment, which may include both sensational and physical tightening without many of the drawbacks of products currently on the market, such as whitening, cracking, and/or peeling.

It was discovered that improved tightening effects and reduced whitening effects may be obtained using skin tightening compositions having the specific compositions discussed herein. For instance, aspects of the invention are directed to a ratio of sodium silicate to magnesium aluminum silicate ranging from 0.08 to 1.0—e.g., 0.08 to 0.9, 0.08 to 0.8, or 0.1 to 1, by weight based on the total weight of the skin-tightening composition. Additionally, aspects of the invention are directed to skin-tightening compositions having a total amount of sodium silicate and magnesium aluminum silicate ranging from 3% to 13%, by weight based on the total weight of the skin-tightening composition. In one instance, the amount of magnesium aluminum silicate may be at least 3%, at least 3.5%, at least 4%, at least 5%, or at least 6%, by weight of the total weight of the skin-tightening composition. The amounts of sodium silicate and magnesium aluminum silicate, individually, in the skin-tightening compositions are further discussed below.

Typically, the skin-tightening compositions of the instant disclosure form an emulsion, such as a water-in-oil emulsion or, preferably, an oil-in-water emulsion. For example, the skin-tightening compositions may be in the form of an oil-in-water emulsion and include:

(a) about 0.1 wt. % to about 6 wt. % of sodium silicate;

(b) at least 3 wt. % to about 11.5 wt. % of magnesium aluminum silicate;

wherein the weight ratio of (a) to (b) is from 0.08 to 1.0 ((a)/(b)) and a total amount of sodium silicate and magnesium aluminum silicate is 3 wt. % to 13 wt. %;

(c) about 1 wt. % to about 15 wt. % of one or more fatty compounds;

(d) about 0.1 to about 20 wt. % of one or more nonionic emulsifiers;

(e) about 1 to about 25 wt. % of one or more polyols; and (f) about 50 to about 90 wt. % of water, wherein the weight percentages are based on the total weight of the composition.

The skin-tightening compositions preferably have a rapid dry time. In some instances, the skin-tightening composition dries in 10 minutes or less, preferably 8 minutes or less, preferably 5 minutes or less, preferably 2 minutes or less, preferably 1 minutes or less, and preferably 30 seconds or less. Additionally, the skin-tightening compositions may provide tightening effects for up to 4 hours, preferably up to 6 hours, preferably up to 8 hours, and preferably up to 10 hours.

The skin-tightening compositions may be formulated to form a transparent film when applied to the skin. The skin-tightening compositions may form a transparent film when applied to the skin before drying of the skin-tightening compositions, after drying of the skin-tightening compositions, or both before and after drying of the skin-tightening compositions. In some instances, the transparent film has a total transmittance of at least 70%, preferably at least 75%, preferably at least 77%, preferably at least 80%, or more preferably at least 82%. In other instances, the transparent film has a total transmittance of about 70% and about 95%, about 75 to about 95%, or about 80% to about 95%. To determine transmittance, the skin-tightening composition can be applied onto a polyester film, such as those sold by the company Byk, using a film spreader to deposit a coat 50 um thick, which is left to dry for about 30 minutes at room temperature (25° C.). The transparency measurements are taken on the dry deposit obtained, using a Hazegard Plus machine from Bye Additive & Instruments.

Suitable components, such as those listed below, may be included or excluded from the formulations for the skin-tightening compositions depending on the specific combination of other components, the form of the skin-tightening compositions, and/or the use of the formulation.

Sodium Silicate

The skin-tightening compositions include an amount sodium silicate typically ranging from about 0.1% to about 6%, by weight based on the weight of the total skin-tightening composition. For example, the amount of the sodium silicate may be present in an amount from about 0.5% to about 20%, about 0.5% to about 18%, about 0.5% to about 16%, about 0.5% to about 14%, about 0.5% to about 12%, about 0.5% to about 10%, about 0.5% to about 8%, from about 1% to about 20%, about 1% to about 18%, about 1% to about 16%, about 1% to about 14%, about 1% to about 12%, about 1% to about 10%, about 1% to about 8%, from about 2% to about 20%, about 2%, about 18%, about 2% to about 16%, about 2% to about 16%, about 2% to about 14%, about 2% to about 12%, about 2% to about 10%, about 2% to about 8%, from about 3% to about 20%, about 3% to about 18%, about 3% to about 16%, about 3% to about 14%, about 3% to about 12%, about 3% to about 10%, about 3% to about 8%, from about 4% to about 20%, about 4% to about 18%, about 4% to about 16%, about 4% to about 14%, about 4% to about 14%, about 4% to about 12%, about 4% to about 10%, about 4% to about 8%, from about 5% to about 20%, about 5% to about 18%, about 5% to about 16%, about 5% to about 14%, about 5% to about 12%, about 5% to about 10%, or about 5% to about 8%, by weight of the total weight of the skin-tightening composition. Additionally or alternatively, the amount of the sodium silicate present in the skin-tightening compositions may be from 1% to 20%, 1% to 18%, 1% to 16%, 1% to 14%, 1% to 12%, 1% to 10%, 1% to 8%, from 2% to 20%, 2%, 18%, 2% to 16%, 2% to 16%, 2% to 14%, 2% to 12%, 2% to 10%, 2% to 8%, from 3% to 20%, 3% to 18%, 3% to 16%, 3% to 14%, 3% to 12%, 3% to 10%, 3% to 8%, from 4% to 20%, 4% to 18%, 4% to 16%, 4% to 14%, 4% to 14%, 4% to 12%, 4% to 10%, 4% to 8%, from 5% to 20%, 5% to 18%, 5% to 16%, 5% to 14%, 5% to 12%, 5% to 10%, or 5% to 8%, by weight of the total weight of the skin-tightening composition.

The sodium silicate may include or be chosen from sodium othosilicate, sodium metasilicate, sodium pyrosilicate, and a mixture thereof. The ratio of $SiO_2$ to the $Na_2O$ for the sodium silicate may vary from 2:1 to 3.75:1. In one instance, the sodium silicate has a ratio of $SiO_2$ to the $Na_2O$ of 2:1 to 3.22:1.

Polyvalent Silicate

The skin-tightening compositions include an amount magnesium aluminum silicate typically ranging from at least 3% to about 11.5%, by weight based on the total weight of the skin-tightening composition. For example, the amount of magnesium aluminum silicate may range from about 3% to about 25%, about 3% to about 23%, about 3% to about 21%, about 3% to about 19%, about 3% to about 17%, about 3% to about 15%, about 3% to about 13%, about 3% to about 11.5%, about 3% to about 10.5%, about 3% to about 9.5%, from about 3.5% to about 25%, about 3.5% to about 23%, about 3.5% to about 21%, about 3.5% to about 19%, about 3.5% to about 17%, about 3.5% to about 15%, about 3.5% to about 13%, about 3.5% to about 11.5%, about 3.5% to about 10.5%, about 3.5% to about 9.5%, from about 4% to about 25%, about 4% to about 23%, about 4% to about 21%, about 4% to about 19%, about 4% to about 17%, about 4% to about 15%, about 4% to about 13%, about 4% to about 11.5%, about 4% to about 10.5%, about 4% to about 9.5%, from about 4.5% to about 25%, about 4.5% to about 23%, about 4.5% to about 21%, about 4.5% to about 19%, about 4.5% to about 17%, about 4.5% to about 15%, about 4.5% to about 13%, about 4.5% to about 11.5%, about 4.5% to about 10.5%, about 4.5% to about 9.5%, from about 5% to about 25%, about 5% to about 23%, about 5% to about 21%, about 5% to about 19%, about 5% to about 17%, about 5% to about 15%, about 5% to about 13%, about 5% to about 11.5%, about 5% to about 10.5%, about 5% to about 9.5%, by weight of the total weight of the skin-tightening composition. Additionally or alternatively, the amount of the magnesium aluminum silicate present in the skin-tightening compositions may be from 3% to 25%, 3% to 23%, 3% to 21%, 3% to 19%, 3% to 17%, 3% to 15%, 3% to 13%, 3% to 11.5%, 3% to 10.5%, 3% to 9.5%, from 3.5% to 25%, 3.5% to 23%, 3.5% to 21%, 3.5% to 19%, 3.5% to 17%, 3.5% to 15%, 3.5% to 13%, 3.5% to 11.5%, 3.5% to 10.5%, 3.5% to 9.5%, from 4% to 25%, 4% to 23%, 4% to 21%, 4% to 19%, 4% to 17%, 4% to 15%, 4% to 13%, 4% to 11.5%, 4% to 10.5%, 4% to 9.5%, from 4.5% to 25%, 4.5% to 23%, 4.5% to 21%, 4.5% to 19%, 4.5% to 17%, 4.5% to 15%, 4.5% to 13%, 4.5% to 11.5%, 4.5% to 10.5%, 4.5% to 9.5%, from 5% to 25%, 5% to 23%, 5% to 21%, 5% to 19%, 5% to 17%, 5% to 15%, 5% to 13%, 5% to 11.5%, 5% to 10.5%, 5% to 9.5%, by weight of the total weight of the skin-tightening composition.

The skin-tightening compositions may include polyvalent silicates in addition to the magnesium aluminum silicate. Examples of polyvalent silicates that that may be suitably incorporated into the skin-tightening composition include or may be chosen from magnesium silicate, calcium silicate, aluminum silicate, a polyvalent silicate clay, montmorillonite, bentonite, smectite, and mixtures thereof.

Fatty Compounds

The skin-tightening composition may include one or more fatty compounds, which may be liquid or solid at room temperature and at atmospheric pressure (25° C., 1 atm). Fatty compounds are typically organic compounds that are not soluble in water at normal temperature (25° C.) and at atmospheric pressure (750 mmHg) (solubility below 10%). In some instances, the solubility in water may be below 5%, below 1%, or below 0.1%.

The total amount of fatty compounds in the skin-tightening compositions may vary from, e.g., about 0.1 to about 25 wt. %, based on the total weight of the composition. For example, the total amount of fatty compounds may be from about 0.1% to about 25%, about 0.1% to about 20%, about 0.1% to about 15%, about 0.1% to about 10%, about 0.1% to about 8%, about 0.1% to about 6%, about 0.1% to about 5%, about 0.1% to about 4%, from about 0.5% to about 25% about 0.5% to about 20%, about 0.5% to about 15%, about 0.5% to about 10%, about 0.5% to about 8%, about 0.5% to about 6% about 0.5% to about 5%, about 0.5% to about 4%, from about 1% to about 25%, about 1% to about 20%, about 1% to about 15%, about 1% to about 10%, about 1% to about 8%, or about 1% to about 6% about 1% to about 5%, about 1% to about 4%, from about 1.5% to about 25%, about 1.5% to about 20%, about 1.5% to about 15%, about 1.5% to about 10%, about 1.5% to about 8%, or about 1.5% to about 6% about 1.5% to about 5%, about 1.5% to about 4%, by weight of the total composition, including ranges and sub-ranges therebetween. Additionally or alternatively, the total amount of fatty compounds may be from 0.1% to 25%, 0.1% to 20%, 0.1% to 15%, 0.1% to 10%, 0.1% to 8%, 0.1% to 6%, 0.1% to 5%, 0.1% to 4%, from 0.5% to 25% 0.5% to 20%, 0.5% to 15%, 0.5% to 10%, 0.5% to 8%, 0.5% to 6% 0.5% to 5%, 0.5% to 4%, from 1% to 25%, 1% to 20%, 1% to 15%, 1% to 10%, 1% to 8%, or 1% to 6% 1% to 5%, 1% to 4%, from 1.5% to 25%, 1.5% to 20%, 1.5% to 15%, 1.5% to 10%, 1.5% to 8%, or 1.5% to 6% 1.5% to 5%, 1.5% to 4%, by weight of the total composition, including ranges and subranges therebetween.

Non-limiting examples of fatty compounds of the skin-tightening composition include or may be chosen from oils, mineral oil, fatty alcohols, fatty acids, fatty alcohol derivatives, fatty acid derivatives (e.g., alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), glyceryl esters (glycerol esters), alkyl ethers of fatty alcohols, fatty acid esters of alkyl ethers of fatty alcohols, fatty acid esters of alkoxylated fatty alcohols, fatty acid esters of alkyl ethers of alkoxylated fatty alcohols, esters of fatty alcohols, hydroxy-substituted fatty acids, waxes, triglyceride compounds, lanolin, and a mixture thereof. In some instances, the one or more fatty compound may comprise or be chosen from fatty alcohols, fatty acids, esters of fatty acids, and/or esters of fatty alcohols (e.g., cetyl palmitate, cetyl stearate, myristyl myristate, myristyl stearate, cetyl myristate, and stearyl stearate (a mixture of which is referred to as "cetyl esters")). Additionally or alternatively, the one or more fatty compounds may include or be chosen from hydrocarbons, fatty alcohols, fatty alcohol derivatives, fatty acids, fatty acid derivatives, fatty esters, fatty ethers, oils, waxes, etc. In one instance, the one or more fatty compounds is a hydrocarbon that is linear, branched, and/or cyclical, such as cyclic $C_6$-$C_{16}$ alkanes, hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

Fatty Alcohols

The one or more fatty compounds may be glycerolated and/or oxyalkylenated, include from 8 to 30 carbon atoms, and/or be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the cosmetic composition may be liquid or solid fatty esters at 25° C., 1 atm. The fatty esters may include esters from a $C_6$-$C_{32}$ fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, cetearyl ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetearyl ethylhexanoate, and mixtures thereof. In yet a further instance, the skin-tightening composition includes one or more of or may have fatty compounds chosen from cetearyl alcohol, cetearyl ethylhexanoate, isopropyl myristate, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof. In one instance, the one or more fatty compounds include at least one of or are selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In another instance, fatty compounds of the skin-tightening composition includes one or more fatty acid triglycerides, such as caprylic/capric triglyceride.

Fatty Alcohol Derivatives

The skin-tightening compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The skin-tightening compositions may, in some instances, include fatty acid derivatives. The fatty acid derivatives are defined herein to include fatty acid esters of the fatty alcohols as defined above, fatty acid esters of the fatty alcohol derivatives as discussed above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

Nonionic Emulsifiers

The skin-tightening compositions include one or more nonionic emulsifiers. The total amount of nonionic emulsifiers in the skin-tightening compositions may vary from, e.g., about 0.1% to about 20%, by weight based on the total weight of the composition. For example, the total amount of nonionic emulsifiers may be from about 0.1% to about 20%, about 0.1% to about 15%, about 0.1% to about 10%, about 0.1% to about 8%, about 0.1% to about 6%, about 0.1% to about 5%, about 0.1% to about 4%, about 0.1% to about 3%, from about 0.5% to about 20%, about 0.5% to about 15%, about 0.5% to about 10%, about 0.5% to about 8%, about 0.5% to 6%, about 0.5% to about 5%, about 0.5% to about 4%, about 0.5% to about 3%, from about 1% to about 20%, about 1% to about 15%, about 1% to about 10%, about 1% to about 8%, or about 1% to about 6%, about 1% to about 5%, about 1% to about 4%, about 1% to about 3%, from about 1.5% to about 20%, about 1.5% to about 15%, about 1.5% to about 10%, about 1.5% to about 8%, or about 1.5% to about 6%, about 1.5% to about 5%, about 1.5% to about 4%, about 1.5% to about 3%, by weight of the total skin-tightening composition, including ranges and sub-ranges therebetween. Additionally or alternatively, the total amount of nonionic emulsifiers may be from 0.1% to 20%, 0.1% to 15%, 0.1% to 10%, 0.1% to 8%, 0.1% to 6%, 0.1% to 5%, 0.1% to 4%, 0.1% to 3%, from 0.5% to 20%, 0.5% to 15%, 0.5% to 10%, 0.5% to 8%, 0.5% to 6%, 0.5% to 5%, 0.5% to 4%, 0.5% to 3%, from 1% to 20%, 1% to 15%, 1% to 10%, 1% to 8%, or 1% to 6%, 1% to 5%, 1% to 4%, 1% to 3%, from 1.5% to 20%, 1.5% to 15%, 1.5% to 10%, 1.5% to 8%, or 1.5% to 6%, 1.5% to 5%, 1.5% to 4%, 1.5% to 3%, by weight of the total skin-tightening composition, including ranges and sub-ranges therebetween.

The nonionic emulsifiers may include or be chosen from emulsifiers, such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof. In some instances, the one or more non-ionic emulsifiers may be chosen from oxyalkylenated organosiloxane emulsifiers. The oxyalkylenated organosiloxane emulsifiers may be fully or partially crosslinked and/or be elastomeric or non-elastomeric. They are sometimes referred to as "emulsifying elastomers" because of they have both elastomeric and emulsifying properties. In some instances, the one or more non-ionic emulsifiers include those chosen from an oganosiloxane emulsifier, including crosslinked organosiloxane emulsifiers. For example, the skin-tightening compositions may comprise one or more crosslinked organosiloxane emulsifier including at least one of or chosen from dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer, and mixtures thereof.

In another instance, the skin-tightening compositions include one or more linear organosiloxane emulsifier(s) chosen from cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone; and mixtures thereof.

The skin-tightening composition may, in some instances, include an oxyalkylenated organosiloxane emulsifier. The oxyalkylenated organosiloxane emulsifier may have a structure in accordance with the following general formula:

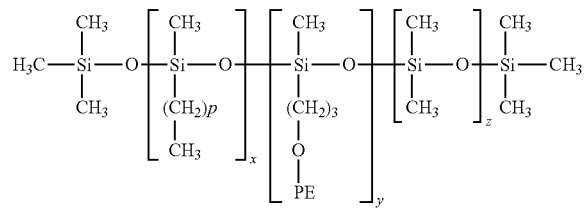

wherein p is 0-40 (the range including all numbers between and subranges such as 2, 3, 4, 13, 14, 15, 16, 17, 18, etc.), and PE is (—C2H4O)a-(—C3H6O)b-H wherein a is 0-25, b is 0-25 with the proviso that both a and b cannot be 0 simultaneously, x, y, and z are each independently ranging from 0 to 1 million with the proviso that x and y cannot be 0 simultaneously. In some instances, x, y, z, a, and b are such that the molecular weight of the polymer ranges from about 5,000 to about 500,000, from about 10,000 to 100,000, or is about 50,000, and the polymer is generically referred to as dimethicone copolyol. In additional instances, p is such that the long chain alkyl is cetyl or lauryl, and the compound is called, generically, cetyl dimethicone copolyol or lauryl dimethicone copolyol respectively. In some cases, the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

The oxyalkylenated organosiloxane emulsifier may alternatively have a structure in accordance with the following general formula:

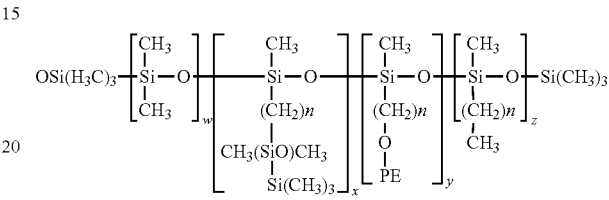

wherein each n is independently 0-100 with the proviso that there must be at least one PE radical. In some instances, where each n independently ranges from about 2 to 30, and PE (—C2H4O)a-(—C3H6O)b-H wherein a is 0-25, b is 0-25 with the proviso that both a and b cannot simultaneously be 0; and wherein w, x, y, and z are each independently 0 to 1,000,000 with the proviso that there is at least one PE. In some embodiments, the organosiloxane emulsifier is lauryl PEG-9 Polydimethylsiloxyethyl Dimethicone. Oxyalkylenated organosiloxane emulsifiers disclosed in U.S. Pat. No. 9,095,543 may be useful in the cosmetic compositions. U.S. Pat. No. 9,095,543 is incorporated herein by reference in its entirety for all purposes.

Further examples of organosiloxane emulsifiers may include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/

18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

The one or more nonionic emulsifiers may, in some instances, be polyoxyalkylenated silicone elastomers, such as, e.g., those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

The polyglycerolated silicone elastomers may include or be chosen from dimethicone/polyglycerin-3 crosspolymer dispersed in dimethicone; or lauryl dimethicone/polyglycerin-3 crosspolymer dispersed in a variety of solvents such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The nonionic emulsifiers may, in some instances, be nonionic a surfactant, such as one chosen from: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Additional nonionic surfactants that may, in some instances, be suitable include, e.g., alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24) alkylpolyglycosides; N—($C_6$-$C_{24}$)alkylglucamine derivatives, amine oxides such as (C10-C14)alkylamine oxides or N—($C_{10}$-$C_{14}$)acylaminopropylmorpholine oxides; and mixtures thereof.

In some cases, the nonionic surfactant may be chosen from esters of polyols with fatty acids with a saturated or unsaturated chain containing for example from 8 to 24 carbon atoms, and alkoxylated derivatives thereof; polyethylene glycol esters of a $C_8$-$C_{24}$; sorbitol esters of a $C_8$-$C_{24}$; sugar (sucrose, glucose, alkylglycose) esters of a $C_8$-$C_{24}$, preferably $C_{12}$-$C_{22}$, fatty acid or acids and alkoxylated derivatives thereof; ethers of sugar and a $C_8$-$C_{24}$, preferably $C_{12}$-$C_{22}$, fatty alcohol or alcohols; and mixtures thereof. In one instance, the nonionic surfactant is an ethoxylated fatty ester chosen from adducts of ethylene oxide with esters of lauric acid, palmitic acid, stearic acid or behenic acid, and mixtures thereof. Examples of ethoxylated fatty esters that may be suitable include those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

Additional nonionic surfactants that may be suitable may include those chosen from glyceryl esters of fatty acids, glyceryl stearate (glyceryl mono-, di- and/or tristearate) (CTFA name: glyceryl stearate); glyceryl ricinoleate; glyceryl esters of $C_8$-$C_{24}$ alkoxylated fatty acids, such as polyethoxylated glyceryl stearate (glyceryl mono-, di- and/or tristearate), and PEG-20 glyceryl stearate; and mixtures thereof.

In one embodiment, the nonionic emulsifier of the skin-tightening composition includes at least one of or is selected from polyglyceryl-based emulsifiers, polyol esters, glycerol ethers, oxyethylenated and/or oxypropylenated ethers, ethylene glycol polymers, sorbitan esters, and a mixture thereof. For example, the nonionic emulsifier may include one or more polyglyceryl-based emulsifiers, such as polyglyceryl 10-stearate, polyglyceryl-3-caprate, polyglyceryl-3-diisostearate, polyglyceryl-3 methylglucose distearate, etc. In one instance, the one or more polyglyceryl-based emulsifiers of the skin-tightening composition are chosen from polyglyceryl 10-stearate, polyglyceryl-3-caprate, polyglyceryl-3-diisostearate, polyglyceryl-3 methylglucose distearate, and a mixture thereof.

Polyol(s)

The skin-tightening composition may include one or more polyols. The one or more polyols may be chosen from polyols having from 2 to 15 carbon atoms and at least two hydroxyl groups. In one instance, the one or more polyols include at least one of or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

Additional polyols that may be used in the skin-tightening composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The one or more polyols may, in some instances, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the skin-tightening composition includes or is chosen from caprylyl glycol, glycerin, and a mixture thereof.

The total amount of polyols in the skin-tightening compositions may vary from, e.g., about 0.1% to about 25%, by weight based on the total weight of the skin-tightening composition. For example, the total amount of polyols may be from about 0.1% to about 25%, about 0.1% to about 20%, about 0.1% to about 15%, about 0.1% to about 10%, about 0.1% to about 8%, about 0.1% to about 6%, from about 1% to about 25%, about 1% to about 20%, about 1% to about 15%, about 1% to about 10%, about 1% to about 8%, about 1% to 6%, from about 2% to about 25%, about 2% to about 20%, about 2% to about 15%, about 2% to about 10%, about 2% to about 8%, or about 2% to about 6%, from about 3% to about 25%, about 3% to about 20%, about 3% to about 15%, about 3% to about 10%, about 3% to about 8%, or about 3% to about 6%, from about 4% to about 25%, about 4% to about 20%, about 4% to about 15%, about 4% to about 10%, about 4% to about 8%, or about 4% to about 6%, including ranges and sub-ranges therebetween, by weight based on the total weight of the skin-tightening composition. Additionally or alternatively, the total amount of polyols may be from 0.1% to 25%, 0.1% to 20%, 0.1% to 15%, 0.1% to 10%, 0.1% to 8%, 0.1% to 6%, from 1% to 25%, 1% to 20%, 1% to 15%, 1% to 10%, 1% to 8%, 1% to 6%, from 2% to 25%, 2% to 20%, 2% to 15%, 2% to 10%, 2% to 8%, or 2% to 6%, from 3% to 25%, 3% to 20%, 3% to 15%, 3% to 10%, 3% to 8%, or 3% to 6%, from 4% to 25%, 4% to 20%, 4% to 15%, 4% to 10%, 4% to 8%, or 4% to 6%, including ranges and sub-ranges therebetween, by weight based on the total weight of the skin-tightening composition.

Water

The total amount of water in the skin-tightening composition can vary, but is typically about 30 to about 95 wt. %, based on the total weight of the skin-tightening composition. In some instances, total amount of water is about 30% to about 90%, about 30% to about 85%, about 30% to about 80.%, about 35% to about 90%, about 35% to about 85%, about 35% to about 80%, about 40% to about 90%, about 40% to about 85%, about 40% to about 80%, about 45% to about 90%, about 45% to about 85%, about 45% to about 80%, about 50% to about 90%, about 50% to about 85%, about 50% to about 80%, about 55% to about 90%, about 55% to about 85%, about 55% to about 80%, about 60% to about 90%, about 60% to about 85%, about 60% to about 80%, about 65% to about 90%, about 65% to about 85%, or about 65% to about 80%, including ranges and sub-ranges therebetween, by weight based on the total weight of the skin-tightening composition.

Thickening Agents

The skin-tightening compositions of the disclosure typically include one or more thickening agent. The amount of thickening agents may depend on the other components in skin-tightening composition and desired viscosity for the skin-tightening composition. For example, the skin-tightening composition may include an amount of thickening agent(s) such that the viscosity of the skin-tightening composition is about 500 cP to about 1,000,000 cP, about 1,000 cP to about 750,000 cP, about 5,000 cP to about 500,000 cP, or about 10,000 cP to about 200,000 cP, at a temperature of 25° C. using a Brookfield rheometer at 20 revolutions per minute (RPM). The thickening agents may be in an amount up to about 20%, about 0.1% to about 10%, about 0.1% to about 9%, about 0.2% to about 9%, about 0.3% to about 9%, about 0.4% to about 8%, about 0.5% to about 5%, about 1% to about 20%, about 1% to about 5%, or about 1% to about 3%, including ranges and sub-ranges therebetween, by weight based on the total weight of the skin-tightening composition.

Suitable thickening agent that may, in some cases, be included in the skin-tightening composition include xanthan gum, guar gum, biosaccharide gum, cellulose, acacia Seneca gum, sclerotium gum, agarose, pechtin, gellan gum, hyaluronic acid. The thickening agent may be a polymeric thickener, such as those chosen from ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, acrylates/beheneth-25 methacrylate copolymer, an acrylates/steareth-20 methacrylate copolymer, and mixtures thereof. In some cases, the thickening agent may be an anionic associative polymeric thickener, such as acrylates/steareth-20 methacrylate copolymer such as Aculyn™ 22 (Dow Chemical Company); acrylates/beneneth-25 methacrylate copolymer such as Novethix™ (Lubrizol); acrylate copolymer such as Carbopol® Aqua SF-1 Polymer (Lubrizol). Many anionic associative polymeric thickeners are water-soluble, and increase the viscosity of water or form an aqueous gel when incorporated into an aqueous composition.

The thickening agents that may be preferably incorporated into the skin-tightening composition include acryloyldimethyltaurate polymers, carboxylic acid polymers, crosslinked polyacrylate polymers, polyacrylamide polymers, polysaccharides, gums, and a mixture thereof. In one instance, the thickening agent includes one or more acryloyldimethyltaurate polymers chosen from acrylamide/sodium acryloyldimethyltaurate copolymer, acrylamide/sodium acryloyldimethyltaurate/acrylic acid copolymer, ammonium acryloyldimethyltaurate/beheneth-25 methacrylate crosspolymer, ammonium acryloyldimethyltaurate/carboxyethyl acrylate crosspolymer, ammonium acryloyldimethyltaurate/laureth-7 methacrylate copolymer, ammonium acryloyldimethyltaurate/steareth-25 methacrylate crosspolymer, ammonium acryloyldimethyltaurate/steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium acryloyldimethyltaurate/Steareth-20 methacrylate copolymer, hydroxyethyl acrylate/Sodium acryloyldimethyl taurate copolymer, polyacryloyldimethyltaurate polyoxymethylene melamine, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate, crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer, sodium polyacryloyldimethyl taurate, and a mixture thereof. In an embodiment, the skin-tightening composition includes an amount of hydroxyethyl acrylate/Sodium acryloyldimethyl taurate copolymer.

Film Former

The skin-tightening composition optionally includes a film former. The film former may be include at least of colloidal silica, pullulan, Polycacrylate-21 (and) acrylates/dimethylaminoethylmethacrylate copolymer, Polyurethanes, polysaccharides, polyvinylpyrrolidone, polyacrylates, acrylates copolymer, and mixtures thereof. In some cases, the film former is a polysaccharide, which may have one or more free hydroxyl groups. In one instance, the polysaccharide is pullulan.

If present, the amount of film former in the skin-tightening composition may range from about 0.1% to about 20%, about 0.1% to about 15%, about 0.1% to about 10%, about 0.1% to about 8%, about 0.1% to about 6%, about 0.1% to about 5%, about 0.1% to about 4%, about 0.1% to about 3%, from about 0.5% to about 20%, about 0.5% to about 15%, about 0.5% to about 10%, about 0.5% to about 8%, about 0.5% to 6%, about 0.5% to about 5%, about 0.5% to about 4%, about 0.5% to about 3%, from about 1% to about 20%, about 1% to about 15%, about 1% to about 10%, about 1% to about 8%, or about 1% to about 6%, about 1% to about 5%, about 1% to about 4%, about 1% to about 3%, from about 1.5% to about 20%, about 1.5% to about 15%, about 1.5% to about 10%, about 1.5% to about 8%, or about 1.5% to about 6%, about 1.5% to about 5%, about 1.5% to about 4%, about 1.5% to about 3%, by weight of the total skin-tightening composition, including ranges and sub-ranges therebetween.

Pigments, Colorants, and Soft Focus Powder

The skin-tightening compositions may optionally include one or more pigments, colorants, and/or soft focus powders. Pigments, colorants, and soft focus powders may be included so that the skin-tightening composition is not clear and/or translucent. The amount of pigments, colorants, and/or soft focus powders included in the skin-tightening composition may vary depending on the product and the desired appearance. Provided below are lists of pigments, colorants, and/or soft focus powders that may be suitably included in some instances of the skin-tightening composition:

Pigments

Non-limiting examples include titanium dioxide, zirconium oxide, cerium oxide, zinc oxide, iron oxide, tin oxide, MICA, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof.

The total amount of pigments, if present, may vary but is typically about 0.01% to about 10%, by weight based on the total weigh of the skin-tightening composition. The total amount of inorganic pigments may be about 0.01% to about 8%, about 0.01% to about 5%, about 0.01% to about 4%, about 0.1% to about 10%, about 0.1% to about 8%, about 0.1% to about 5%, or about 0.1% to about 4%, by weight based on the total weight of the skin-tightening composition.

Colorants

Non-limiting examples include D & C red no. 19 (CI 45,170), D & C red no. 9 (CI 15,585), D & C red no. 21 (CI 45,380), D & C orange no. 4 (CI 15,510), D & C orange no. 5 (CI 45,370), D & C red no. 27 (CI 45,410), D & C red no. 13 (CI 15,630), D & C red no. 7 (CI 15,850:1), D & C red no. 6 (CI 15,850:2), D & C yellow no. 5 (CI 19,140), D & C red no. 36 (CI 12,085), D & C orange no. 10 (CI 45,425), D & C yellow no. 6 (CI 15,985), D & C red no. 30 (CI 73,360), D & C red no. 3 (CI 45,430), carbon black (CI 77,266), cochineal carmine lake (CI 75,470), natural or synthetic melanin, and aluminium lakes.

The total amount of colorants, if present, may vary but is typically about 0.01% to about 10%, by weight based on the total weigh of the skin-tightening composition. The total amount of coloarants may be about 0.01% to about 8%, about 0.01% to about 5%, about 0.01% to about 4%, about 0.1% to about 10%, about 0.1% to about 8%, about 0.1% to about 5%, or about 0.1% to about 4%, by weight based on the total weight of the skin-tightening composition.

Soft Focus Powder

The skin-tightening compositions may optionally include a soft focus powder. Soft focus powders are materials providing a blurring effect, typically due to their light-scattering properties on the skin. Such powders typically have high diffuse reflectance, low specular reflectance, and high diffuse transmittance. Soft focus powders give the skin a smoother appearance, for example, by reducing the difference in luminosity between the valley and the edges of wrinkles and imperfections.

Non-limiting examples of soft focus powders include powders of natural or synthetic origin such as mica, titanated mica, alumina, titanium dioxide, serecite, composite talc/titanium dioxide/alumina/silica powders, polyamide, poly(methyl (meth)acrylate), polyethylene powder, polymethylsilsesquioxane powder, sodium acrylates crosspolymer-2 and a mixture thereof. Additional non-limiting examples include calcium aluminum borosilicate (LUXSIL), PMMA (Microsphere M-100), polyethylene (POLYETHYLENE CI 2080), methyl methacrylate crosspolymer (COVABEADS LH85), nylon-12 (ORGASOL 2002), or ethylene/acrylic acid copolymer (FLOBEADS EA209). In some instances, the skin-tightening compositions include at least one soft focus powder selected from the group consisting of silica which may or may not be coated, fumed silica, silica silylate, composite talc/titanium dioxide/alumina/silica powders, polyamide (nylon), poly(methyl (meth)acrylate), polyethylene powder, polymethylsilsesquioxane powder, waxes, such as copernicia cerifera (carnauba) wax, dimethicone/vinyl dimethicone crosspolymer, nylon-12, cellulose, polylactic acid, boron nitride, and a mixture thereof. The copernicia cerifera (carnauba) wax can be provided as a dispersion non water and alcohol. The dimethicone/vinyl dimethicone crosspolymer can be provided as silicone dispersion (INCI: Dimethicone/vinyl dimethicone crosspolymer (and) C12-14 Pareth-12). In some instances, the soft focus powder is (or includes) sodium acrylates crosspolymer-2, which is commercially available as AQUAKEEP 10SH-NFC as sodium acrylates crosspolymer-2 (and) water (and) silica.

The total amount of soft focus powder, if present, can vary but is typically about 0.1% to about 20%, by weight based on the total weight of the skin-tightening composition. In some cases, the total amount of soft focus powder is about 0.1% to about 15%, about 0.1% to about 10%, about 0.1% to about 5%, about 1% to about 20%, about 1% to about 15%, about 1% to about 10%, or about 1% to about 10%, by weight based on the total weight of skin-tightening composition.

Active Ingredients

The skin-tightening compositions described herein may, optionally, include one or more active ingredients. The skin-tightening compositions may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

Non-limiting examples of the one or more active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In one some instances, the skin-tightening composition includes an active ingredient such as a humectant and moisturizing ingredients, an anti-aging agent, a depigmenting agent, an anti-wrinkle agent, or an agent that treats oily skin.

Humectants and moisturizing ingredients may be glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (Actinidia chinensis) marketed by Gattefosse, an extract of Paeonia suffruticosa root, such as that sold by Ichimaru Pharcos under the name Liquid Botanpi Be an extract of brown sugar (Saccharum officinarum) such as molasses extract marketed by Taiyo Kagaku under the name Liquid Molasses, without this list being exhaustive. Particular depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (Actinidia chinensis) marketed by Gattefosse, an extract of Paeonia suffruticosa root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

pH Adjuster

The skin-tightening composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The skin-tightening composition may include one or more bases, such as sodium hydroxide, potassium hydroxide and the like, to decrease the pH of the cosmetic composition. Additional or alternative acids and bases that are suitable for adjusting the pH of the skin-tightening composition are readily known to one of ordinary skill in the art.

The amount of the pH adjuster in the skin-tightening composition may be based on the desired pH of the final cosmetic composition and/or product. For example, the total amount of the pH adjuster may range from about 0.05% to about 20%, based on the total weight of the skin-tightening composition. In some instances, the total amount of pH adjuster is from about 0.05% to about 15%, about 0.5% to about 10%, about 1% to about 5%, about 1.5% to about 4%, or about 2.0% to about 3%, by weight of the total weight of the skin-tightening composition, including ranges and subranges therebetween. Additionally or alternatively, the cosmetic compositions may include an amount of pH adjuster ranging from 0.05% to 15%, 0.5% to 10%, 1% to 5%, 1.5% to 4%, or 2.0% to 3%, by weight of the total weight of the skin-tightening composition, including ranges and subranges therebetween.

The compositions of the present disclosure may be in the form of a liquid dispersion, a gel, a cream, a lotion, a mousse, or a spray. The composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The instant disclosure also relates to methods for improving the appearance of skin by applying the skin-tightening compositions described herein to the skin. The methods may improve the appearance of skin by treating or reducing the appearance of, e.g., wrinkles, blemishes, dryness, roughness, dullness, age spots, sagging, eye bags, and/or puffy skin.

Additionally, the instant disclosure relates to methods for firming and/or tightening the skin by applying the skin-tightening compositions described herein to the skin and forming a skin-tightening film or layer on the skin. In some instances, the skin tightening compositions are applied to the skin of the face, and/or more specifically around the eyes, around the mouth, and/or around the neck.

Embodiments

In certain embodiments, the skin-tightening compositions of the instant disclosure optionally form an oil-in-water emulsion and include:
  about 0.1 wt. % to about 6 wt. %, preferably about 0.5 wt. % to about 5.5 wt. %, of sodium silicate, such as those chosen from sodium othosilicate, sodium metasilicate, sodium pyrosilicate, and a mixture thereof;
  at least 3 wt. % to about 11.5 wt. %, preferably about 3.5 wt. % to about 10% of magnesium aluminum silicate;
  the weight ratio of sodium silicate to magnesium aluminum silicate is from 0.08 to 1.0, preferably 0.08 to 0.9, and a total amount of sodium silicate and magnesium aluminum silicate is 3 wt. % to 13 wt. %, preferably 3.5 wt. % to 12.5 wt. %;
  about 1 wt. % to about 15 wt. %, preferably about 1 wt. % to 10 wt. %, more preferably about 1 wt. % to about 5 wt. % of one or more fatty compounds, such as those chosen from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof;
  about 0.1 wt. % to about 20 wt. %, preferably about 1 wt. % to 10 wt. %, more preferably about 1 wt. % to about 5 wt. % of one or more nonionic emulsifiers, such as those chosen from polyglyceryl-based emulsifiers, polyol esters, glycerol ethers, oxyethylenated and/or oxypropylenated ethers, ethylene glycol polymers, sorbitan esters, and a mixture thereof;

about 1 wt. % to about 25 wt. %, preferably about 2 wt. % to about 15 wt. %, more preferably about 3 wt. % to about 10 wt. % of one or more polyols, such as those having from 2 to 15 carbon atoms and at least two hydroxyl groups; and about 50 wt. % to about 90 wt. %, preferably about 55 wt. % to about 85 wt. % of water, wherein all of the weight percentages are based on the total weight of the skin-tightening composition.

In additional embodiments, the skin-tightening compositions of the instant disclosure form an oil-in-water emulsion and include:

about 0.1 wt. % to about 6 wt. %, preferably about 0.5 wt. % to about 5.5 wt. %, of sodium silicate, such as those chosen from sodium othosilicate, sodium metasilicate, sodium pyrosilicate, and a mixture thereof;

at least 3 wt. % to about 11.5 wt. %, preferably about 3.5 wt. % to about 10%, of magnesium aluminum silicate;

the weight ratio of sodium silicate to magnesium aluminum silicate is from 0.08 to 1.0, preferably 0.08 to 0.9, and a total amount of sodium silicate and magnesium aluminum silicate is 3 wt. % to 13 wt. %, preferably 3.5 wt. % to 12.5 wt. %;

about 1 wt. % to about 5 wt. %, preferably about 1.5 wt. % to about 4 wt. %, of one or more fatty acids of triglycerides, such as, e.g., caprylic/capric triglyceride;

about 0.1 wt. % to about 5 wt. %, preferably about 0.5 wt. % to about 4 wt. %, more preferably about 0.5 wt. % to about 3 wt. %, of one or more polyglyceryl-based emulsifiers, including, for example, polyglyceryl-3 methylglucose distearate;

about 1 wt. % to about 25 wt. %, preferably about 2 wt. % to about 15 wt. %, more preferably about 3 wt. % to about 10 wt. %, of one or more polyols having from 2 to 15 carbon atoms and at least two hydroxyl groups, the one or more polyols being chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof;

about 50 wt. % to about 90 wt. %, preferably about 55 wt. % to about 85 wt. % of water; and about 0.1 wt. % to about 10 wt. %, preferably about 0.2 wt. % to about 9 wt. %, more preferably about 0.5 wt. % to about 5 wt. %, of one or more acryloyldimethyltaurate polymers, such as those chosen from acrylamide/sodium acryloyldimethyltaurate copolymer, acrylamide/sodium acryloyldimethyltaurate/acrylic acid copolymer, ammonium acryloyldimethyltaurate/beheneth-25 methacrylate crosspolymer, ammonium acryloyldimethyltaurate/carboxyethyl acrylate crosspolymer, ammonium acryloyldimethyltaurate/laureth-7 methacrylate copolymer, ammonium acryloyldimethyltaurate/steareth-25 methacrylate crosspolymer, ammonium acryloyldimethyltaurate/steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium acryloyldimethyltaurate/Steareth-20 methacrylate copolymer, hydroxyethyl acrylate/Sodium acryloyldimethyl taurate copolymer, polyacryloyldimethyltaurate polyoxymethylene melamine, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate, crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer, sodium polyacryloyldimethyl taurate, and a mixture thereof, wherein all of the weight percentages are based on the total weight of the skin-tightening composition.

EXAMPLES

The following non-limiting examples are provided primarily for the purposes of elucidating the benefits and properties achieved by aspects of the invention. Fifteen skin-tightening compositions were prepared in accordance with the formulations provided in Table 1, shown on the following page. Examples A-E have compositions prepared in accordance with aspects of the invention. Comparative Examples F-P were prepared according to the same procedures as Examples A-E, but have formulations that are outside the desired ranges for one or more aspects of the invention.

Examples A-E and Comparative Examples G-P were assessed to determine the tightening effect of the formulations and the level of whitening effect of the formulations after a specified amount of time. Specifically, about 2 ml of the skin-tightening compositions of Examples A-E and Comparative Examples G-P were applied with a consistent sweeping motion to sections of skin in the under eye area. After 10 minutes, the skin-tightening compositions of Examples A-E and Comparative Examples G-P had dried and the whitening effect was evaluated. Photos were then taken of the under eye sections of skin with the skin-tightening compositions of Examples A-E and Comparative Examples G-P thereon. The photos were assessed by an expert to determine the amount of tightening effect and the amount of whitening effect associated with each of the skin-tightening compositions.

The expert evaluated each of the skin-tightening compositions of Examples A-E and Comparative Examples G-P on a scale from 1-5 based on the levels of whitening on a Fitzpatrick IV skin tone scale. For example, a value of 1 was assigned when no whitening effect was exhibited and a value of 5 was assigned when the extremely noticeable whitening effect was exhibited. The amount of tightening effect was evaluated in a similar manner 10 minutes after application of the skin-tightening compositions to the skin. The expert evaluated the tightening effect for each of the skin-tightening compositions of Examples A-E and Comparative Examples G-P on a scale from 1 to 5. The skin-tightening compositions that exhibited the largest tightening effect were assigned a 5 and the skin-tightening compositions that exhibited no tightening effect were assigned a 1. The scales both for the whitening effect and the tightening effect were used to compare skin-tightening compositions against each other and were representative of this sample size.

TABLE 1

| | Components | | Examples | | | | | Comparative Examples | | | | | | | | | |
|---|---|---|---|---|---|---|---|---|---|---|---|---|---|---|---|---|---|
| | | | A | B | C | D | E | F | G | H | I | K | L | M | N | O | P |
| (a) | Sodium Silicate | SODIUM SILICATE | 3 | 3 | 0.5 | 5.3 | 0.5 | 7.6 | 5.3 | 7.6 | 0.5 | 10 | 0.5 | 10 | 7.6 | 5.3 | 2.9 |
| (b) | Polyvalent Silicate | MAGNESIUM ALUMINUM SILICATE | 3.8 | 9.3 | 6.5 | 6.5 | 3.8 | 3.8 | 1 | 1 | 1 | 3.8 | 12 | 1 | 6.5 | 3.8 | 12 |
| Ratio of (a)/(b) | | | 0.8 | 0.3 | 0.08 | 0.8 | 0.1 | 2 | 5.3 | 7.6 | 0.5 | 2.6 | 0.04 | 10 | 0.7 | 1.4 | 0.2 |
| Total amount of (a) and (b) | | | 6.8 | 12.3 | 7.0 | 11.8 | 4.3 | 11.4 | 6.3 | 8.6 | 1.5 | 13.8 | 12.5 | 11 | 14.1 | 9.1 | 14.9 |
| (c) | Fatty Comp. | CAPRYLIC/CAPRIC TRIGLYCERIDE | 2 | 2 | 2 | 2 | 2 | 2 | 2 | 2 | 2 | 2 | 2 | 2 | 2 | 2 | 2 |
| (d) | Nonionic Emulsifiers | POLYGLYCERYL-3 METHYLGLUCOSE DISTEARATE | 1 | 1 | 1 | 1 | 1 | 1 | 1 | 1 | 1 | 1 | 1 | 1 | 1 | 1 | 1 |
| (e) | Polyol | GLYCERIN | 5 | 5 | 5 | 5 | 5 | 5 | 5 | 5 | 5 | 5 | 5 | 5 | 5 | 5 | 5 |
| (f) | | WATER | QS | QS | QS | QS | OS | QS | QS | QS | QS | QS | QS | QS | QS | QS | QS |
| Tightening | | | 3 | 5 | 4 | 4 | 3 | 3 | 1 | 4 | 1 | 3 | 4 | 1 | 3.5 | 4 | 5 |
| Whitening | | | 2 | 3 | 1 | 2 | 2 | 5 | 1 | 5 | 1 | 5 | 5 | 3 | 5.5 | 4 | 4 |

Comparative Examples G, H, I, and M were formulated to have 1 wt. % of magnesium aluminum silicate. Comparative Examples G, H, I, and M exhibited a low amount of tightening effect in comparison to the amount of whitening effect. Specifically, Comparative Examples G and I provided insufficient amounts of tightening effect and exhibited an amount of whitening effect that was proportional to the tightening effect based on the scale employed for Table 1. Comparative Examples H and M contained significantly more sodium silicate than Comparative Examples G and I and, thus, exhibited greater tightening effects. However, Comparative Examples H and M exhibited whitening effects that were greater than the tightening effects based on the scale employed for Table 1.

Comparative Examples F, K, and O had a ratio of the sodium silicate amount to magnesium aluminum silicate amount that was greater than the desired range of aspects of the invention. Comparative Example O was identified as a Comparative Example because the ratio of the sodium silicate amount to magnesium aluminum silicate amount was outside the desired range of aspects of the invention. Interestingly, Comparative Example O exhibited an undesirable amount of whitening effect and exhibited an amount of whitening effect that was proportional to the tightening effect based on the scale employed for Table 1.

Comparative Example F had a formulation similar to Comparative Example O, except that Comparative Example F had a greater amount of sodium silicate. Surprisingly, Comparative Example F exhibited a lower amount of tightening effect as compared to Comparative Example O, although Comparative Example F had a greater amount of sodium silicate. Without intending to be limited by any one theory, it is believed that the ratio of the sodium silicate to magnesium aluminum silicate affects the amount of tightening effect exhibited by the skin-tightening compositions. Comparative Example F also exhibited a greater amount of whitening effect than Comparative Example O.

Comparative Example K had a formulation similar to Comparative Examples O and F, except that Comparative Example K had more sodium silicate than Comparative Examples O and F. The total amount for both the sodium silicate and the magnesium aluminum silicate was outside the desired range of aspects of the invention. Comparative Example K exhibited undesirable amounts of whitening effect and exhibited a greater amount whitening effect than tightening effect based on the scale used for Table 1.

Comparative Examples N and P had formulations that included a total amount of both sodium silicate and magnesium aluminum silicate that was greater than the desired range of aspects of the invention. Comparative Example N also had an amount of sodium silicate that was outside the desired range of aspects of the invention. Comparative Example N exhibited undesirable amounts of whitening effect and exhibited a greater amount whitening effect that the tightening effect based on the scale used for Table 1. Comparative Example P had an amount of magnesium aluminum silicate that was outside the desired range for aspects of the invention. Comparative Example P provided sufficient tightening effect, but undesirable amounts of whitening effect.

Comparative Example L had a formulation that was similar to Comparative Example P, but had less sodium silicate and, thus, a total amount of sodium silicate and magnesium aluminum silicate that was within the desired range of aspects of the invention. However, Comparative Example L had an amount of magnesium aluminum silicate and a ratio of the sodium silicate to the magnesium aluminum silicate that was outside the desired range of aspects of the invention. Surprisingly, the whitening effect exhibited by Comparative Example L was greater than that of Comparative Example P, even though Comparative Example L was formulated with less sodium silicate than Comparative Example P.

Generally, Examples A-E exhibited a greater amount of the tightening effect while simultaneously exhibiting a reduced amount of whitening effect as compared to Comparative Examples F-P. Examples A-E each exhibited an amount of whitening effect of 3 or less and exhibited an amount of tightening effect of 3 or more. Desirably, each of Examples A-E exhibited an amount of tightening effect that was greater than the amount of whitening effect based on the scale employed by Table 1.

As discussed above, it is commonly expected that skin tightening compositions having greater than 1 wt. % of magnesium aluminum silicate are prone to cracking and whitening effects. Surprisingly, Examples A-E, which included more than 1 wt. % of magnesium aluminum silicate, produced greater amounts of tightening effect while exhibiting suitable amounts of whitening effect.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the cosmetic compositions of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as skin, in particular, the skin of the head, face, and neck.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

The invention claimed is:

1. A skin-tightening composition in the form of an oil-in-water emulsion comprising:
    (a) about 0.1 wt. % to about 6 wt. % of sodium silicate;
    (b) at least 5 wt. % to about 11.5 wt. % of magnesium aluminum silicate;
        wherein the weight ratio of (a) to (b) is 0.08 to 0.8 ((a)/(b)) and a total amount of sodium silicate and magnesium aluminum silicate is 5.1 wt. % to 13 wt. %;
    (c) about 1 wt. % to about 15 wt. % of one or more fatty compounds;
    (d) about 0.1 to about 20 wt. % of one or more nonionic emulsifiers;
    (e) about 1 to about 25 wt. % of one or more polyols, wherein the one or more polyols are chosen from polyols having from 2 to 15 carbon atoms and at least two hydroxyl groups; and
    (f) about 50 to about 90 wt. % of water,
        wherein the weight percentages are based on the total weight of the composition.

2. The skin-care composition of claim 1, wherein the sodium silicate of (a) is chosen from sodium othosilicate, sodium metasilicate, sodium pyrosilicate, and a mixture thereof.

3. The skin-tightening composition of claim 1, wherein the one or more fatty compounds of (c) are chosen from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof.

4. The skin-tightening composition of claim 1, wherein the one or more fatty compounds of (c) include one or more fatty acid triglycerides.

5. The skin-tightening composition of claim 4, wherein the one or more fatty acid triglycerides includes caprylic/capric triglyceride.

6. The skin-tightening composition of claim 1, wherein the one or more nonionic emulsifiers of (d) are chosen from polyglyceryl-based emulsifiers, polyol esters, glycerol ethers, oxyethylenated and/or oxypropylenated ethers, ethylene glycol polymers, sorbitan esters, and a mixture thereof.

7. The skin-tightening composition of claim 1, wherein the one or more nonionic emulsifiers of (d) includes one or more polyglyceryl-based emulsifiers.

8. The skin-tightening composition of claim 7, where in the one or more polyglyceryl-based emulsifiers are chosen from polyglyceryl 10-stearate, polyglyceryl-3-caprate, polyglyceryl-3-diisostearate, polyglyceryl-3 methylglucose distearate, and a mixture thereof.

9. The skin-tightening composition of claim 1, wherein the one or more polyols are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

10. The skin-tightening composition of claim 1 further comprising:
(g) one or more thickening agents.

11. The skin-tightening composition of claim 10, wherein the one or more thickening agents are chosen from acryloyldimethyltaurate polymers, carboxylic acid polymers, crosslinked polyacrylate polymers, polyacrylamide polymers, polysaccharides, gums, and a mixture thereof.

12. The skin tightening composition of claim 10, wherein the one or more thickening agents includes one or more acryloyldimethyltaurate polymers chosen from acrylamide/sodium acryloyldimethyltaurate copolymer, acrylamide/sodium acryloyldimethyltaurate/acrylic acid copolymer, ammonium acryloyldimethyltaurate/beheneth-25 methacrylate crosspolymer, ammonium acryloyldimethyltaurate/carboxyethyl acrylate crosspolymer, ammonium acryloyldimethyltaurate/laureth-7 methacrylate copolymer, ammonium acryloyldimethyltaurate/steareth-25 methacrylate crosspolymer, ammonium acryloyldimethyltaurate/steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium acryloyldimethyltaurate/Steareth-20 methacrylate copolymer, hydroxyethyl acrylate/Sodium acryloyldimethyl taurate copolymer, polyacryloyldimethyltaurate polyoxymethylene melamine, sodium acrylate/acryloyldimethyltaurate/dimethyl acrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate, crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer, sodium polyacryloyldimethyl taurate, and a mixture thereof.

13. The skin-tightening composition of claim 1 formulated to form a transparent film when applied to skin.

14. A skin-tightening composition in the form of an oil-in-water emulsion comprising:
(a) about 0.1 wt. % to about 6 wt. % of sodium silicate;
(b) at least 5 wt. % to about 11.5 wt. % of magnesium aluminum silicate;
  wherein the weight ratio of (a) to (b) is from 0.08 to 0.8 ((a)/(b)) and a total amount of sodium silicate and magnesium aluminum silicate is 3 wt. % to 13 wt. %;
(c) about 1 wt. % to about 5 wt. % of one or more fatty acids of triglycerides;
(d) about 0.1 wt. % to about 5 wt. % of one or more polyglyceryl-based emulsifiers;
(e) about 1 wt. % to about 25 wt. % of one or more polyols chosen from polyols having from 2 to 15 carbon atoms and at least two hydroxyl groups;
(f) about 50 wt. % to about 90 wt. % of water; and
(g) about 0.1 wt. % to about 10 wt. % of one or more acryloyldimethyltaurate polymers;
  wherein the weight percentages are based on the total weight of the composition.

15. A method for improving the appearance of skin comprising applying the composition of claim 1 to the skin.

16. The methods of claim 15, wherein improving the appearance of skin comprises treating or reducing the appearance of wrinkles, blemishes, dryness, roughness, dullness, age spots, sagging, eye bags, and/or puffy skin.

17. A method for firming and/or tightening the skin comprising applying the composition of claim 1 to the skin.

* * * * *